US012734131B2

(12) United States Patent
Breitkreutz et al.

(10) Patent No.: US 12,734,131 B2
(45) Date of Patent: Sep. 15, 2026

(54) LOSARTAN-CONTAINING MICRO TABLET FOR PEDIATRIC APPLICATIONS

(71) Applicant: Midas Pharma GmbH, Ingelheim (DE)

(72) Inventors: Joerg Breitkreutz, Haltern am See (DE); Valentine Lura, Teningen (DE)

(73) Assignee: Midas Pharma GmbH, Ingelheim (DE)

( * ) Notice: Subject to any disclaimer, the term of this patent is extended or adjusted under 35 U.S.C. 154(b) by 186 days.

(21) Appl. No.: 18/559,440

(22) PCT Filed: May 9, 2022

(86) PCT No.: PCT/EP2022/062409
§ 371 (c)(1),
(2) Date: Nov. 7, 2023

(87) PCT Pub. No.: WO2022/234139
PCT Pub. Date: Nov. 10, 2022

(65) Prior Publication Data

US 2024/0238206 A1 Jul. 18, 2024

(30) Foreign Application Priority Data

May 7, 2021 (EP) .................................... 21172815

(51) Int. Cl.
*A61K 9/20* (2006.01)
*A61K 9/28* (2006.01)
*A61K 31/4178* (2006.01)

(52) U.S. Cl.
CPC .......... *A61K 9/2072* (2013.01); *A61K 9/2009* (2013.01); *A61K 9/2027* (2013.01); *A61K 9/2054* (2013.01); *A61K 9/2866* (2013.01); *A61K 31/4178* (2013.01)

(58) Field of Classification Search
None
See application file for complete search history.

(56) References Cited

FOREIGN PATENT DOCUMENTS

EP 2 836 207 A1 2/2015
WO WO 2013/154390 10/2013
WO WO-2013154390 A1 * 10/2013 .............. A61P 37/08
WO WO-2020213868 A1 * 10/2020 ........... A61K 9/4808

OTHER PUBLICATIONS

Alfred C. F. Rumondor et al., "Minitablets: Manufacturing, Characterization Methods, and Future Opportunities", *American Pharmaceutical Review,* Merck & Co, Jul. 30, 2016.

* cited by examiner

*Primary Examiner* — Susan T Tran
(74) *Attorney, Agent, or Firm* — Smith Patent, LLC; Chalin A. Smith

(57) ABSTRACT

The present invention relates to mini tablets for pediatric applications containing losartan or one of its pharmaceutically acceptable salts.

17 Claims, 4 Drawing Sheets

Figure 1. Comparison of Sizes of Mini Tablets according to the Invention

Figure 2. SEM Cross-Section
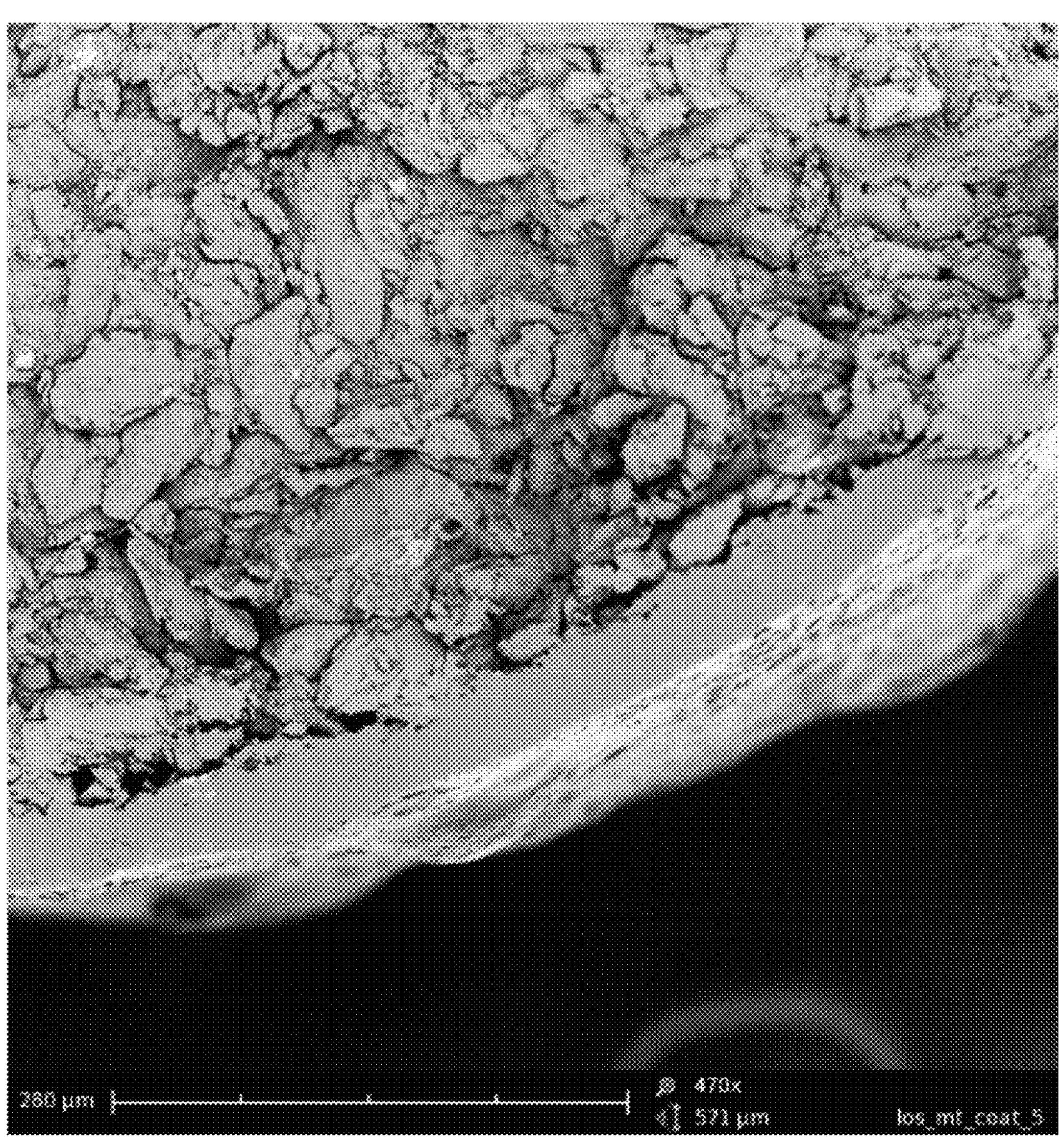

Figure 3. Micro Computer Tomography (μCT) Cross-Section
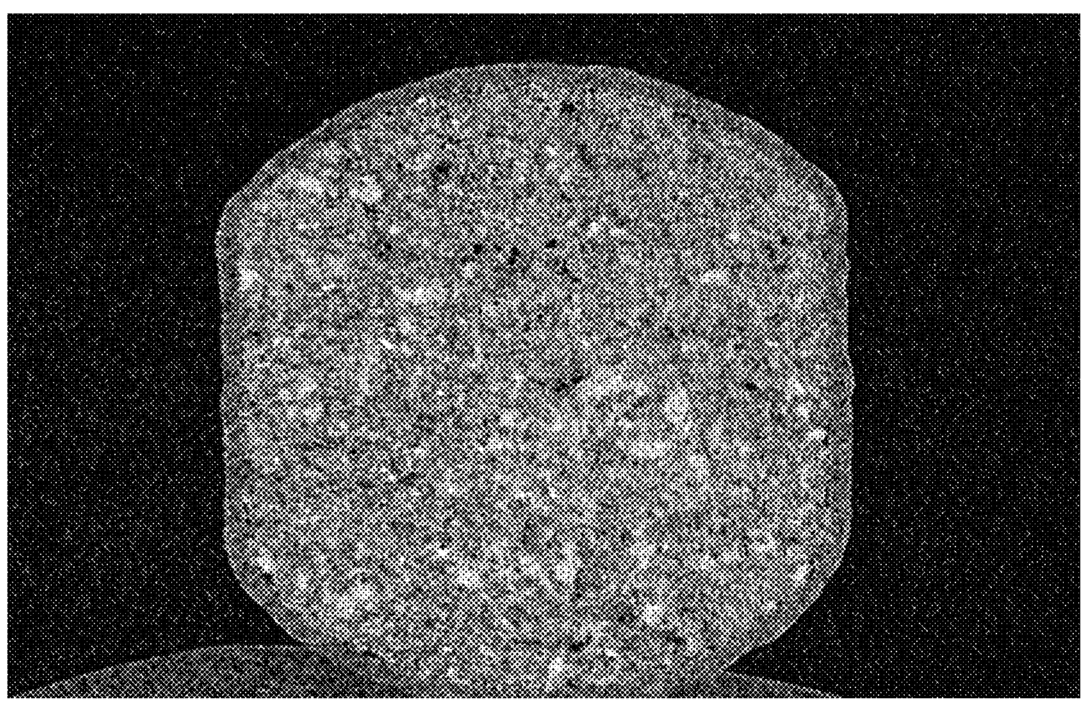

Figure 4. Active Ingredient Release
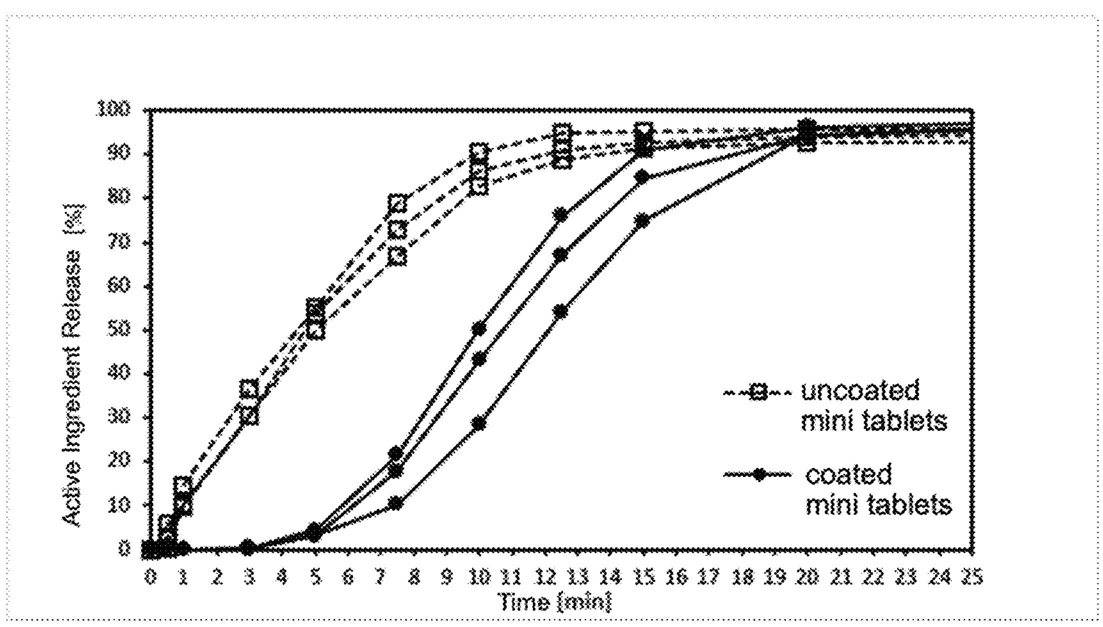

LOSARTAN-CONTAINING MICRO TABLET FOR PEDIATRIC APPLICATIONS

PRIORITY

This application corresponds to the U.S. National phase of International Application No. PCT/EP2022/062409, filed May 9, 2022, which, in turn, claims priority to European Patent Application No. 21172815.9 filed May 7, 2021, the contents of which are incorporated by reference herein in their entirety.

BRIEF DESCRIPTION OF THE PRESENT INVENTION

Losartan is the international nonproprietary name, INN, for 2-butyl-4-chloro-1-[[2'-(1H-tetrazole-5-yl)[1,1'-biphenyl]-4-yl]methyl]-1H-imidazole-5-methanol.

Losartan blocks the interaction of angiotensin II and its receptor and is primarily employed for the treatment of hypertension, cardiac insufficiency, ischemic peripheral circulatory disturbance, myocardial ischaemia (angina pectoris), diabetic neuropathy, and glaucoma, as well as for preventing progression of cardiac insufficiency after myocardial infarct. Additionally, losartan is approved for the treatment of the essential hypertension, namely both in adults and children and adolescent aged 6 to 18.

Additionally, an advantageous effect of losartan was shown in the treatment of diseases such as for example the Marfan's syndrome, the imperfect osteogenesis (osteogenesis imperfecta, OI), or also fibrotic diseases such as Epidermolysis bullosa, EB. Generally, many of these diseases already occur in children and therefore, treatment has to start in childhood.

Accordingly, a losartan-containing dosage form suitable for pediatric application has to fulfil the requirement that the dose of the therapeutic agent increases with the children, i.e., can be adapted in possibly small steps.

A form of administration of losartan potassium in the form of a 2.5 mg/ml powder as well as solvent for the preparation of a suspension for taking that is for pediatric application was approved in 2014 under the tradename LORZAAR®.

Said formulation in addition to the active ingredient losartan has a plurality of further components, namely a powder containing microcrystalline cellulose (E460), lactose monohydrate, pre-gelatinized corn starch, vegetable magnesium stearate (E572), and Opadry WHITE consisting of hyprolose (E463), hypromellose (E464), and titania (E171), and a solvent containing microcrystalline cellulose (E460), carmellose sodium, citric acid, water, xanthan gum (E415), methyl-4-hydroxybenzoate (E218), sodium dihydrogen phosphate monohydrate, potassium sorbate, carrageenan, calcium sulphate, sodium phosphate, glycerole, sweet beery lemon flavour, propyl-4-hydroxybenzoate (E216), sodium citrate, saccharine sodium, sorbitol (E420), and a defoaming AF emulsion consisting of water, dimeticone, glycerol mono/di [-palmitate, -stearate], macrogol stearate, and macrogol.

According to the LORZAAR® technical information the recommended daily initial dose of losartan potassium for patients aged 6 to 18 years is 0.7 mg/kg which in case of a body weight between 20 kg and 50 kg corresponds to a daily dose of 14 g to 35 mg of active ingredient.

SUMMARY OF THE PRESENT INVENTION

The LORZAAR® suspension has several drawbacks. In order to keep it stable preservatives must be added. Moreover, an accurate dosage is quite complicated and hardly possible without further excipients. Suspensions tend to sedimentation and therefore, must be agitated again and again when used several times. To mask the taste of the extremely bitter tasting losartan both the viscosity enhancers carrageenan and xanthan gum and several sweeteners and flavours are added.

One problem of the present invention can be seen in providing a losartan-containing oral dosage form which is suitable for pediatric application and which avoids the drawbacks of the dosage forms known in the prior art.

This problem is solved by the losartan-containing mini tablets described in the following.

The mini tablets according to the present invention suitable for pediatric applications contain losartan or one of its pharmaceutically acceptable salts. By the low active ingredient content the mini tablets according to the invention are advantageous in that they are suitable both for exactly individually adjusting and incrementally increasing the dose, i.e., allow a flexible adaption of the dosage to the changing body weight of children, namely by giving whole units.

For example, for a child with 20 kg body weight the daily dose of 0.7 mg of losartan per kg body weight to be administered is 14 mg of losartan which corresponds to 14 mini tablets a 1 mg, 10 mini tablets à 1.4 mg, or 7 mini tablets à 2 mg.

An increase of the body weight by only 2 kg can be taken into account by giving an additional mini tablet à 1.4 mg.

For an easier dosage mini tablets according to the present invention can be administered via individually adjustable dosing dispensers. Therefore, an aspect of the invention relates to a kit comprising 50 to 2000 losartan mini tablets according to the invention as well as a dosing dispenser.

The mini tablets according to the invention have a ratio of surface area to volume of 2:1 to 6:1 $mm^{-1}$.

The mass of the mini tablets preferably is 3 mg to 15 mg, preferably 4 mg to 10 mg, particularly preferred 5 mg to 9 mg.

Moreover, preferred mini tablets according to the invention have a diameter and a height of 1 mm to 3 mm, further preferred of 1.5 mm to 2.5 mm. This creates another advantage, namely that of an improved swallowability of said plurality of small dimensioned and thus easily swallowable units. Moreover, mini tablets having a diameter of up to 3 mm can already safely be applied with children from the age of two.

A further advantage of the mini tablets according to the invention is the improved physical and chemical stability compared to a suspension, so that no preservatives must be added.

BRIEF DESCRIPTION OF THE FIGURES

FIG. 1 presents a comparison of sizes of the mini tablets prepared in accordance with the present invention.

FIG. 2 presents an SEM image of a cross-section of a mini tablet coated with 5 $mg/cm^2$ of polymer.

FIG. 3 presents a micro-computertomography image (µCT) of a cross-section of a mini tablet coated with 10 $mg/cm^2$ of polymer.

FIG. 4 graphically compares the release of active ingredient over time in uncoated mini tablets and coated mini tablets prepared in accordance with the present invention.

DETAILED DESCRIPTION OF THE PREFERRED EMBODIMENTS

The pharmaceutical mini tablets of the present invention contain the active ingredient losartan preferably in the form of a salt, preferably the potassium salt, wherein each unity contains a single dose of 0.5 mg to 4 mg, preferably 1 mg to 3 mg of the active ingredient.

Losartan, due to the small dimensions of mini tablets, must be contained in relatively large proportions. In addition, mini tablets have an increased surface area-to-volume ratio. Since losartan has a poor fluidity and strongly tends to clot the tools during formulation the development of mini tablets with a large proportion of losartan poses a particular challenge, besides additionally particular attention must be paid to a good fluidity of the formulations in their preparation due to the smaller template openings.

The pharmaceutical mini tablets of the present invention in addition to the active ingredient contain one or more excipients, for example one or more fillers, one or more binders, one or more decomposition accelerators, or/and one or more lubricants.

Pharmaceutically acceptable fillers according to the present invention comprise cellulose derivatives such as microcrystalline cellulose (MCC), methyl cellulose, starches, sugar alcohols such as mannitol, sorbitol, or xylitol, acrylate polymers and copolymers, dextrates, dextrine, dextrose, maltodextrine, pectin, and gelatine. A preferred filler is silicified microcrystalline cellulose. The total amount of fillers is in the range of 20 wt. % to 80 wt. %, preferably in the range of 30 wt. % to 60 wt. %, based on the total weight of the composition.

Pharmaceutically acceptable binders according to the present invention comprise vinylpyrrolidone vinylacetate copolymers (copovidone), hydroxypropyl cellulose (HPC), dihydroxypropyl cellulose, hydroxyethyl cellulose, polymethacrylates, sodium alginate, polyvinylpyrrolidone (povidone), pre-gelatinized starch, and mixtures thereof. A preferred binder is copovidone. The total amount of binder is in the range of 0.5 wt. % to 10 wt. %, preferably in the range of 3 wt. % to 7 wt. %, based on the total weight of the composition.

Pharmaceutically acceptable decomposition accelerators according to the present invention comprise crospovidone, croscarmellose, carboxymethyl cellulose, carboxymethyl starch, and mixtures thereof. A preferred decomposition accelerator is crospovidone. The total amount of decomposition accelerator is in the range of 1 wt. % to 10 wt. %, preferably in the range of 1 wt. % to 4 wt. %, based on the total weight of the composition.

Pharmaceutically acceptable lubricants according to the present invention comprise talc, magnesium stearate, calcium stearate, sodium stearate, stearic acid, hexanedioic acid, sodium stearyl fumarate, glycerine fumarate, and mixtures thereof. Preferred lubricants are magnesium stearate and talc. The total amount of lubricant is in the range of 1 wt. % to 5 wt. %, preferably in the range of 2 wt. % to 4 wt. %, based on the total weight of the composition.

Furthermore, the mini tablets according to the invention can optionally contain brittle excipients in order to increase the compressive strength of the tablet during compression. Pharmaceutically acceptable brittle excipients according to the present invention comprise calcium phosphate, tricalcium citrate, mannitol, sucrose, xylitol, and lactitol as well as mixtures thereof. A preferred brittle excipient is dicalcium phosphate anhydrate. The total amount of brittle excipients, if present, is in the range of 10 wt. % to 30 wt. %, preferably in the range of 15 wt. % to 25 wt. %, based on the total weight of the composition.

The LORZAAR® suspension known from the prior art in addition to sweeteners contains the viscosity enhancers carrageenan and xanthan gum. Said excipients contribute to taste masking by increasing the viscosity of the suspension and thus, prolong the time the active ingredient needs to reach the taste receptors on the tongue. In other words, in this way, the contact of the active ingredient to the taste receptors on the tongue before swallowing is reduced. However, this kind of taste masking is reserved to liquid dosage forms such as suspensions and thus, cannot be applied with the solid dosage forms according to the invention.

The inventors of the present application have found that for pediatric formulations of losartan that not only tastes extremely unpleasant, but also is very good soluble, it is of advantage to achieve a physical barrier around the losartan for an optimum taste masking. Thus, the mini tablets according to the invention can have a physical barrier that retards the release of the losartan and ideally suppresses the bitter taste until the mini tablet has been swallowed by the patient.

According to the invention the physical barrier consists of a coating that initially retards the release of the active ingredient. The coating preferably consists of a pharmaceutically acceptable, water-soluble film-forming agent.

Film-forming agents according to the invention comprise polymers such as hydroxypropyl methyl cellulose, methyl cellulose, hydroxypropyl cellulose, hydroxyethyl cellulose, carmellose, polyvinyl pyrrolidone, polyvinyl alcohol, or gastric juice-soluble coatings of polyacrylic acid derivatives such as copolymers of butyl methacrylate, methyl methacrylate, and dimethylaminoethyl methacrylate.

A preferred film-forming agent according to the present invention is the water-soluble polymer hydroxypropyl methyl cellulose (HPMC).

Additionally, the coatings can optionally contain plasticizers, for example polyethylene glycol (PEG).

Film-forming agents and plasticizers preferably are employed in a ratio of 20:1 to 5:1, preferably of 12:1 to 8:1.

For pediatric applications it is generally sufficient to retard the release of the losartan from the mini tablet by one minute. It has been found that the retardation of the active ingredient release correlates with the thickening of the coating.

So, the result was a coat (mass loading) of 5 mg/cm$^2$ in a layer thickness of the coating of 35 μm to 45 μm and by a retardation of the active ingredient release by one minute. In case of twice the amount of a coating, i.e., 10 mg/cm$^2$, the layer thickness of the coating was 75±10 μm and the release of the losartan from the mini tablets in a worth mentioning amount accordingly was only after two minutes.

Therefore, a further aspect of the present invention relates to losartan-containing mini tablets as well as a coating, wherein the release of the losartan in a worth mentioning amount at the earliest takes place after 30 seconds after administration of the dosage form, preferably at the earliest after between 1 minute and 5 minutes, particularly preferred after between 2 minutes and 5 minutes.

A further aspect of the present invention relates to losartan-containing mini tablets as well as a coating, wherein the thickness of the coating is between 20 μm and 100 μm, preferably between 35 μm and 85 μm, and particularly preferred between 65 μm and 85 μm.

For taste masking and improvement, respectively of the mini tablets according to the invention also complexing agents such as for example cyclodextrines or ion exchangers, lipoproteins of high affinity to the taste receptors such as for example adenosine monophosphate as well as taste-improving agents such as sweeteners and flavours can be added.

The mini tablets according to the invention can be prepared in accordance with a method in which in a first step a granulate of losartan as well as one or more fillers is prepared. In a second step the granulate obtained in the first step is mixed with one or more binders and one or more decomposition accelerators. Optionally, the binder can also already be contained in the granulate. In a third step one or more lubricants are added to the mixture obtained in the second step. In the fourth step the mixture is compressed to tablet cores and in a fifth step the tablet cores are coated. Further details on the manufacturing method are mentioned in the examples.

The mini tablets according to the invention are particularly suitable for pediatric applications such as the treatment of essential hypertension, Marfan's syndrome, osteogenesis imperfecta, and fibrotic diseases since the mini tablets according to the invention ensure both a low initial dose and an adaption of the dose to the body weight in small units. A preferred use is the treatment of Epidermolysis bullosa, wherein the mini tablets contain 1 mg to 2 mg, preferably 1.3 mg to 1.7 mg of losartan potassium.

A further preferred embodiment of the present invention relates to a mini tablet for pediatric applications with a ratio of surface area to volume of 2:1 to 6:1 $mm^{-1}$ which contains losartan or one of this pharmaceutically acceptable salts, one or more excipients and a coating, whereby the release of the active ingredient after taking is retarded by 30 seconds or more.

A further preferred embodiment of the present invention relates to a mini tablet for pediatric applications with a ratio of surface area to volume of 2:1 to 6:1 $mm^{-1}$, that contains 0.5 mg to 4 mg of losartan or one of its pharmaceutically acceptable salts, 20 wt. % to 80 wt. % of one or more fillers and a coating containing one or more film-forming agents, whereby the release of the active ingredient after taking is retarded by between 1 and 5 minutes.

A further preferred embodiment of the present invention relates to a mini tablet for pediatric applications with a ratio of surface area to volume of 2:1 to 6:1 $mm^{-1}$, a total weight of 3 mg to 15 mg, that contains 1 mg to 3 mg of losartan or one of its pharmaceutically acceptable salts, 20 wt. % to 80 wt. % of one or more fillers, 0.5 wt. % to 10 wt. % of one or more binders, 1 wt. % to 10 wt. % of one or more decomposition accelerators, 1 wt. % to 5 wt. % of one or more lubricants and a coating containing one or more polymers and optionally one or more plasticizers, whereby the release of the active ingredient after taking is retarded by between 1 and 5 minutes.

A further preferred embodiment of the present invention relates to a mini tablet for the treatment of Epidermolysis bullosa with a ratio of surface area to volume of 2:1 to 6:1 $mm^{-1}$, a total weight of 5 mg to 8 mg and a diameter and a height each of 1.5 mm to 2.5 mm that contains 1.3 mg to 1.7 mg of losartan potassium, 30 wt. % to 60 wt. % of microcrystalline cellulose, 3 wt. % to 7 wt. % of copovidone, 1 wt. % to 4 wt. % of crospovidone, 2 wt. % to 4 wt. % of a mixture of magnesium stearate and talc and a coating consisting of hydroxypropylmethyl cellulose (HPMC), whereby the release of the active ingredient after taking is retarded by between 2 and 4 minutes.

Example 1

In a first step losartan potassium (42.7%) and silicified microcrystalline cellulose (57.3%) are mixed and a dry granulate is prepared by means of a roller press.

Here, the particle size of the granulate is one of the factors influencing its fluidity. In general, the fluidity increases with an increasing particle size, wherein particles larger than 250 μm are considered as free-flowing, particles smaller than 100 μm as cohesive and particles smaller than 10 μm as extremely cohesive.

Table 1 shows that the mean particle size increases with an increasing specific compacting strength (SCS). In case of a granulate compacted with an SCS of 6 kN/cm only 10% of all particles are smaller than 100 μm. The particle size determination was carried out with a Camsizer XT, wherein it was dispersed with compressed-air (x-jet, dispersing pressure: 30 kPa, digital image processing with a two-camera system; measuring range 1 μm-3 mm).

TABLE 1

| Particle Diameter of the Granulate | | | |
|---|---|---|---|
| | SCS = 2 kN/cm | SCS = 4 kN/cm | SCS = 6 kN/cm |
| Mean Particle Diameter [mm] | | | |
| $D_{10}$ | 59 ± 1 | 75 ± 1 | 101 ± 14 |
| $D_{50}$ | 634 ± 12 | 799 ± 8 | 832 ± 12 |
| $D_{90}$ | 1135 ± 4 | 1183 ± 4 | 1204 ± 4 |

Thus, a preferred embodiment of the present invention relates to a losartan-containing granulate characterized in that only 10% of all particles ($D_{10}$) are smaller than 100 μm.

A further parameter for the flow behaviour is the so-called Hausner ratio. Here, the flow behaviour is the better, the smaller the Hausner ratio is, see tab. 2. A 3-fold determination of the Hausner ratio in accordance to Ph. Eur. 2.9.36 for granulates prepared at an SCS of 6 kN/cm yielded a Hausner ratio of 1.33±0.03 which certainly corresponds to a moderate flow behaviour, but under the given difficult general conditions is to be considered as sufficient.

TABLE 2

| Hausner Ratio in accordance with Ph. Eur. 2.9.36 | | |
|---|---|---|
| Flow Behaviour | Hausner Ratio | Compressibility Index |
| excellent | 1.00-1.11 | 1-10% |
| good | 1.12-1.18 | 11-15% |
| satisfactory | 1.19-1.25 | 16-20% |
| moderate | 1.26-1.34 | 21-25% |
| bad | 1.35-1.45 | 26-31% |
| very bad | 1.46-1.59 | 32-37% |
| insufficient | >1.60 | >38% |

Thus, a preferred embodiment of the present invention relates to the preparation of a losartan-containing mini tablet from a granulate with a Hausner ratio of 1.34 or less.

In a second step at first the granulate obtained in step 1 is mixed with the copovidone and the crospovidone. Subsequently, magnesium stearate and talc are added and the resulting mixture is tableted with a rotary press, wherein screening steps can be carried out from time to time, if needed. The composition of the resulting mini tablets is illustrated in table 3.

TABLE 3

| Composition of the mini tablets | | | |
|---|---|---|---|
| Material | Function | Amount [mg] per unit | Amount [%] |
| Losartan Potassium | Active Ingredient | 2.50 | 38.46 |
| Silicified Microcrystalline Cellulose | Filler | 3.34 | 51.54 |
| Copovidone | Binder | 0.33 | 5.00 |
| Crospovidone | Decomposition Accelerator | 0.13 | 2.00 |
| Magnesium Stearate | Lubricant | 0.13 | 2.00 |
| Talc | | 0.07 | 1.00 |
| | Total: | 6.50 | 100 |

In order to withstand the subsequent coating step, the mini tablets must have a sufficient breaking strength. The breaking strength increases with an increasing compacting pressure at which the mini tablets are tableted. Here, the mini tablets according to the invention already at a compacting pressure of 100 MPa had a sufficient breaking strength of about 0.9 MPa. Thus, a further preferred embodiment of the present invention relates to losartan-containing mini tablets which have a mean breaking strength of 0.9 MPa or higher.

The friability also can be used as a parameter to evaluate the mechanical properties of mini tablets. Thus, a test on friability of the mini tablets according to the invention was carried out in accordance with Ph. Eur. 2.9.7. Here, the mini tablets exhibited a friability of 0.14±0.03% which is far below the limit of 1.0% in accordance with the European Pharmacopoeia. Thus, a further preferred embodiment of the present invention relates to losartan-containing mini tablets which have a friability of less than 1%, preferably a friability of less than 0.5%, even more preferred a friability of less than 0.2%.

The average active ingredient content of mini tablets according to the invention was determined in accordance with Ph. Eur. 2.9.40.

TABLE 4

| Active Ingredient Content of the Mini Tablets (n = 10) | | | | |
|---|---|---|---|---|
| Mean [%] | s [%] | rsd [%] | Acceptance Value | Limit (Ph. Eur. 2.9.40) |
| 100.8 | 4.8 | 4.7 | 11.5 | 15 |

Table 4 shows that taking into account the standard deviation the mean content of losartan is within the acceptance values given by the Pharmacopoeia.

The uncoated mini tablets obtained in step 2 in a third step are coated by means of bottom-spray in the fluidized bed. The coating solution in addition to demineralized water contains 12 wt. % of hydroxypropyl methylcellulose (HPMC) and 1.2 wt. % of polyethylene glycol (PEG 6000). A heating step is followed by the spraying process with a subsequent drying step. The instrument settings for the coating process are illustrated in table 5.

TABLE 5

| Coating Process - Instrument Settings | |
|---|---|
| Instrument | Mycrolab-Fluidgerät (Hüttlin, Germany) |
| Inner Diameter of the Nozzle | 0.8 mm |
| Spraying Pressure | 1.0 bar |
| Microclimate | 0.15-0.25 bar |
| Inlet Air Temperature | 48° C. |
| Inlet Air Amount | 13 $m^3$/hr |
| Pumping Rate | 1.3 g/min |

Some parameters of the thus prepared mini tablets are set forth in table 6.

TABLE 6

| Dimensions of the Mini Tablets (n = 20) | | |
|---|---|---|
| Diameter [mm] | Height [mm] | Mass [mg] |
| 2.15 ± 0.01 | 2.21 ± 0.03 | 7.96 ± 0.32 |

FIG. 1 shows a comparison of sizes of the thus prepared mini tablets.

The dissolution studies of the thus prepared mini tablets were carried out in phosphate buffer, pH 6.0, at 37±0.5° C. with a basket apparatus in accordance with Ph. Eur. The active ingredient release was measured by means of HPLC with UV-VIS detector.

As shown in FIG. 4, the release of the active ingredient from uncoated mini tablets virtually takes place immediately. On the other hand, the release profiles of coated mini tablets exhibit an initial retardation of the active ingredient release. In this way the bitter taste of losartan over the time, in which the mini tablets remain in the mouth of the patient, can be avoided compared to the uncoated mini tablets.

The initial retardation of the active ingredient release increases with an increasing polymer coating. A mass loading of 5 mg/cm$^2$ corresponding to a layer thickness of the coating of 35 μm to 45 μm resulted in a retardation of the release of the losartan of more than one minute. In case of a mass loading of about 10 mg/cm$^2$ corresponding to a layer thickness of the coating of 75±10 μm the active ingredient was released with a retardation of more than two minutes.

The SEM image of a cross-section of a mini tablet coated with 5 mg/cm$^2$ of polymer in FIG. 2 and the micro-computertomography image (μCT) of a cross-section of a mini tablet coated with 10 mg/cm$^2$ of polymer in FIG. 3 each show a uniform coating with a complete and intact film.

As is also coming from FIG. 4, there is no retardation going beyond the initial retardation, so that more than 90% of the active ingredient are equally released both from coated and uncoated mini tablets after 20 minutes.

Thus, the coating according to the invention ensures a taste-masking effect that can elegantly be controlled via mass loading and layer thickness, respectively of the coating.

As is coming from table 7, the coated mini tablets according to the invention have very good storage stability. Coated mini tablets were stored under different packaging conditions (open, polyethylene (PE), and aluminum foil (Alu)) for 6 months under two different standard conditions and subsequently the contaminations were determined in accordance with USP 39 Monograph on losartan tablets as follows:

TABLE 7

| Stability Data | | | | | | |
|---|---|---|---|---|---|---|
| | 6 M 25° C./60% r.h. | | | 6 M 40° C./75% r.h. | | |
| Contaminant | Open | PE | Alu | Open | PE | Alu |
| "1H Dimer" | ND | ND | ND | <0.1% | <0.1% | <0.1% |
| "2H Dimer" | ND | ND | ND | ND | ND | <0.1% |
| Other Contaminants | ND | ND | ND | <0.1% | <0.1% | ND |
| Sum of unknown Contaminants | <0.1% | 0.10% | <0.1% | 0.11% | 0.13% | 0.13% |
| Total Contaminants | <0.1% | 0.10% | <0.1% | 0.11% | 0.13% | 0.13% |

Example 2

TABLE 8

| Composition of the Mini Tablets | | | |
|---|---|---|---|
| Material | Function | Amount per Mini Tablet | Proportion [%] |
| Losartan Potassium | Active ingredient | 1.5 | 27.27% |
| Silicified microcrystalline Cellulose | Filler | 2.16 | 39.27% |
| Dicalcium Phosphate Anhydrate | Brittle Excipient | 1.3 | 23.64% |
| Copovidone | Binder | 0.26 | 4.73% |
| Crospovidone | Decomposition Accelerator | 0.11 | 2.00% |
| Magnesium Stearate | Lubricant | 0.11 | 2.00% |
| Talc | | 0.06 | 1.09% |
| | Total: | 5.5 mg | 100.00 |

Mini tablets according to the invention are prepared by mixing in a first step losartan, silicified microcrystalline cellulose, calcium phosphate and copovidone and preparing a dry granulate by means of a roller press. In a further step the dry granulate obtained in step 1 is mixed with crospovidone. Subsequently, magnesium stearate and talc are added in two separate mixing steps. The resulting mixture is tableted on a rotary press. The obtained mini tablets are coated by means of bottom-spray in the fluidized bed. On the composition of the spraying solution see example 1. A heating step is followed by a spraying process with a subsequent drying step.

The mini tablets according to example 2 due to the active ingredient content are particularly suitable for application in the treatment of Epidermolysis bullosa.

The invention claimed is:

1. A mini tablet for pediatric applications which contains an active ingredient selected from among losartan and its pharmaceutically acceptable salts, wherein said mini tablet is characterized by a ratio of surface area to volume that ranges from 2:1 to 6:1 $mm^{-1}$, wherein said mini tablet contains 1 mg to 3 mg of said active ingredient, wherein said mini tablet is characterized by a total weight of 3 mg to 15 mg, and wherein said mini tablet is characterized by a diameter and a height, each of which ranges from 1 mm to 3 mm.

2. The mini tablet for pediatric applications according to claim 1, wherein said mini tablet further comprises one or more fillers selected from the group consisting of microcrystalline cellulose (MCC), methyl cellulose, starches, sugar alcohols, dextrates, dextrine, dextrose, maltodextrine, pectin, and gelatine.

3. The mini tablet for pediatric applications according to claim 1, wherein said mini tablet further comprises one or more binders selected from the group consisting of vinylpyrrolidone vinylacetate copolymers ("copovidone"), hydroxypropyl cellulose ("HPC"), dihydroxypropyl cellulose, hydroxyethyl cellulose, polymethacrylates, sodium alginate, polyvinyl pyrrolidone ("povidone"), and pre-gelatinized starch.

4. The mini tablet for pediatric applications according to claim 1, wherein said mini tablet further comprises one or more decomposition accelerators selected from the group consisting of crospovidone, croscarmellose, carboxymethyl cellulose, and carboxymethyl starch.

5. The mini tablet for pediatric applications according to claim 1, wherein said mini tablet further comprises one or more lubricants selected from the group consisting of magnesium stearate, talc, calcium stearate, sodium stearate, stearic acid, hexanedioic acid, sodium stearyl fumarate, calcium behenate, sodium glyceryl behenate, and glycerine fumarate.

6. The mini tablet for pediatric applications according to claim 1, wherein said mini tablet further comprises a coating that retards release of the active ingredient by 1 minute or more.

7. The mini tablet for pediatric applications according to claim 6, wherein the coating contains one or more polymers.

8. The mini tablet for pediatric applications according to claim 6, wherein the thickness of the coating ranges from 20 mm to 100 mm.

9. The mini tablet for pediatric applications according to claim 1, wherein said mini tablet is formulated for the treatment of essential hypertension, Marfan's syndrome, osteogenesis imperfecta, or fibrotic disease in pediatric patients.

10. The mini tablet for pediatric applications according to claim 9, wherein the fibrotic disease is Epidermolysis bullosa and the mini tablet contains from 1 mg to 2 mg of said active ingredient.

11. A kit for individually adjusting the dose of an active ingredient to a pediatric patient comprising a dosing dispenser and 50 to 2000 mini tablets for pediatric applications according to claim 1.

12. A process for the preparation of a mini tablet according to claim 1, said method comprising the process steps of:

i. preparing a granulate of losartan or one of its pharmaceutically acceptable salts, at least one or more fillers, and optionally further excipients;

ii. mixing the granulate obtained in step (i) with one or more decomposition accelerators and optionally one or more excipients;

iii. mixing the mixture obtained in step (ii) with one or more lubricants and optionally one or more excipients;

iv. compressing the mixture obtained in step (iii) into mini tablets; and v. optionally coating the mini tablets obtained in step (iv).

13. The mini tablet for pediatric applications according to claim 1, wherein said mini tablet is characterized by a total weight of 5 mg to 8 mg.

14. The mini tablet for pediatric applications according to claim 1, wherein said mini tablet is characterized by a diameter and a height, each of which ranges from 1.5 mm to 2.5 mm.

15. The mini tablet for pediatric applications according to claim 1, wherein said mini tablet further comprises one or more sugar alcohol fillers selected from the group consisting of mannitol, sorbitol, and xylitol.

16. The mini tablet for pediatric applications according to claim 6, wherein the thickness of the coating ranges from 65 mm and 85 mm.

17. The mini tablet for pediatric applications according to claim 9, wherein the mini tablet contains 1.3 mg to 1.7 mg of losartan potassium.

* * * * *